United States Patent
Robinson et al.

(10) Patent No.: US 12,161,793 B2
(45) Date of Patent: Dec. 10, 2024

(54) FLUID INGRESS PROTECTION FOR NPWT DEVICE

(71) Applicant: Solventum Intellectual Properties Company, Maplewood, MN (US)

(72) Inventors: Timothy Mark Robinson, San Antonio, TX (US); Christopher Brian Locke, San Antonio, TX (US); Colin J. Hall, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 18/375,842

(22) Filed: Oct. 2, 2023

(65) Prior Publication Data
US 2024/0024563 A1    Jan. 25, 2024

Related U.S. Application Data

(62) Division of application No. 16/570,789, filed on Sep. 13, 2019, now Pat. No. 11,806,466.
(Continued)

(51) Int. Cl.
*A61M 1/00* (2006.01)
*A61F 13/00* (2024.01)
*A61F 13/05* (2024.01)

(52) U.S. Cl.
CPC ....... *A61M 1/784* (2021.05); *A61F 13/00055* (2013.01); *A61F 13/05* (2024.01);
(Continued)

(58) Field of Classification Search
CPC ............ A61M 1/90; A61M 1/86; A61M 1/84; A61M 1/912; A61M 1/913; A61M 39/10; A61M 39/1011; A61F 13/0005
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Leslie A Lopez
*Assistant Examiner* — Seth Han

(57) ABSTRACT

A negative pressure wound treatment (NPWT) system including a NWPT therapy unit and a wound dressing configured to overlay a wound bed. The NPWT system includes a first length of tubing comprising a first end and a second end, the first end of the first length of tubing coupled to the NWPT therapy unit and the second end of the first length of tubing having a first coupling half, as well as a second length of tubing having a first end and second end, the first end of the second length of tubing coupled to the wound dressing and the second end of the second length of tubing having a second coupling half. The NPWT system includes an inline filter comprising a sintered polymer and a superabsorbent material, and an inline coupling, wherein the inline coupling is configured to operably couple and de-couple the NPWT therapy unit and wound dressing.

8 Claims, 3 Drawing Sheets

Related U.S. Application Data

(60) Provisional application No. 62/848,380, filed on May 15, 2019, provisional application No. 62/732,220, filed on Sep. 17, 2018.

(52) U.S. Cl.
CPC ............... *A61M 1/82* (2021.05); *A61M 1/91* (2021.05); *A61M 1/915* (2021.05); *A61M 1/982* (2021.05); *A61M 1/985* (2021.05); *A61M 2205/0238* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,702,665 B2 * | 4/2014 | Locke ................. A61F 13/05 604/319 |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,370,731 B2 * | 6/2016 | Mao ..................... B01D 15/20 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2014/0163491 A1 | 6/2014 | Schuessler et al. |
| 2015/0051560 A1 * | 2/2015 | Askem .................. A61M 1/74 604/319 |
| 2015/0080788 A1 | 3/2015 | Blott et al. |
| 2015/0250974 A1 * | 9/2015 | Bobo, Sr. ............. A61M 39/10 600/543 |
| 2017/0189236 A1 * | 7/2017 | Locke ............... A61F 13/01029 |
| 2018/0256878 A1 * | 9/2018 | Ciccone ............... A61M 39/10 |

FOREIGN PATENT DOCUMENTS

| | | |
|---|---|---|
| AU | 755496 B2 | 12/2002 |
| CA | 2005436 A1 | 6/1990 |
| DE | 2640413 A1 | 3/1978 |
| DE | 4306478 A1 | 9/1994 |
| DE | 29504378 U1 | 9/1995 |
| EP | 0100148 A1 | 2/1984 |
| EP | 117632 A2 | 9/1984 |

(56) References Cited

FOREIGN PATENT DOCUMENTS

| | | | |
|---|---|---|---|
| EP | 161865 | A2 | 11/1985 |
| EP | 358302 | A2 | 3/1990 |
| EP | 1018967 | A1 | 7/2000 |
| GB | 692578 | A | 6/1953 |
| GB | 2195255 | A | 4/1988 |
| GB | 2197789 | A | 6/1988 |
| GB | 2220357 | A | 1/1990 |
| GB | 2235877 | A | 3/1991 |
| GB | 2329127 | A | 3/1999 |
| GB | 2333965 | A | 8/1999 |
| JP | 4129536 | B2 | 8/2008 |
| SG | 71559 | | 4/2002 |
| WO | 80/02182 | A1 | 10/1980 |
| WO | 8704626 | A1 | 8/1987 |
| WO | 90010424 | A1 | 9/1990 |
| WO | 93009727 | A1 | 5/1993 |
| WO | 94020041 | A1 | 9/1994 |
| WO | 9605873 | A1 | 2/1996 |
| WO | 9718007 | A1 | 5/1997 |
| WO | 9913793 | A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, p. 24.

Egnell Minor: Addition to the Users Manual Concerning Overflow Protection—Concerns all Egnell Pumps, Feb. 3, 1983, p. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, The Use of Hypermia in the Postoperative Treatment of Lesions of the Extremities and Thorax, Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians; Jul. 2007.

* cited by examiner

FLUID INGRESS PROTECTION FOR NPWT DEVICE

CROSS-REFERENCE TO RELATED APPLICATIONS

This application claims the benefit of priority to U.S. Provisional Application No. 62/848,380, filed on May 15, 2019, and U.S. Provisional Application No. 62/732,220, filed on Sep. 17, 2018, which are each incorporated herein by reference in their entirety.

BACKGROUND

The present disclosure relates generally to a negative pressure wound therapy (NPWT) device. The present disclosure relates more specifically to protecting a NPWT device from fluid ingress.

Negative pressure wound therapy (NPWT) involves applying negative pressure (relative to atmospheric pressure) to a wound site to promote healing. Typically, a wound dressing is sealed over a wound bed and air is pumped out of the dressing to create a negative pressure at the wound bed. In some NPWT systems, fluid is pumped out of the dressing or instilled into the dressing while negative pressure is applied to the wound site.

Wounds are known to produce fluid at the wound site. NPWT is also known facilitate fluid exudation from wound sites and can subsequently draw fluid in in the direction of a NPWT device. NPWT devices can be damaged and/or contaminated by contact with such fluids. Commonly, tubing for NPWT systems is manipulated due to movement of a patient, with high-profile fluid ingress protection systems easily damaged, disrupted, or displaced due to said manipulation. As such, it is desirable to provide cost-efficient and disposable low-profile fluid ingress protection between the wound site and the NPWT device so as to prevent fluid ingress from the wound site to the NPWT device and maintain functionality through normal patient movement patterns.

SUMMARY

At least one embodiment relates to a negative pressure wound therapy (NPWT) system including a NWPT therapy unit and a wound dressing configured to overlay a wound bed. The NPWT system also includes a first length of tubing having a first end and a second end, with the first end of the first length of tubing coupled to the NPWT therapy unit and the second end of the first length of tubing having a first coupling half. The NPWT system also includes a second length of tubing having a first end and second end, with the first end of the second length of tubing coupled to the wound dressing and the second end of the second length of tubing having a second coupling half. Additionally, the NPWT system includes an inline filter including a sintered polymer and a superabsorbent material and an inline coupling, with the inline coupling comprising a first coupling half and a second coupling half, wherein the inline coupling is configured to operably couple and de-couple the NPWT therapy unit to the wound dressing.

Another embodiment relates to a NPWT system wherein the filter includes a mixture of polyethylene and a super absorbing polymer, and is configured to perform as a gel-block when wet so as to prevent fluid from migrating through the filter.

Another embodiment relates to a NPWT system wherein the first coupling half comprises a female connector and the second coupling half comprises a male connector.

Another embodiment relates to a NPWT system wherein the wherein the inline filter is disposed within the inline coupling.

Another embodiment relates to a NPWT system wherein the filter is disposed within the second coupling half.

Another embodiment relates to a NPWT system wherein the inline filter further comprises a dye configured to be released when wet so as to indicate exposure of the inline filter to fluid.

Another embodiment relates to a NPWT system wherein the filter further comprises activated charcoal as a mixture or a layer.

At least one embodiment relates to a dressing assembly, with the dressing assembly including a wound dressing configured to overlay a wound bed, a length of tubing coupled to the wound dressing, and a filter including a sintered polymer and a superabsorbent material disposed within the tubing.

Another embodiment relates to a dressing assembly wherein the filter comprises a mixture of polyethylene and a super absorbing polymer, and is configured to perform as a gel-block when wet so as to prevent fluid from migrating through the filter.

Another embodiment relates to a dressing assembly including an inline coupling disposed within the tubing, with the filter disposed within the coupling.

Another embodiment relates to a dressing assembly wherein the coupling comprises a first half and a second half and the filter is disposed within either the first half or the second half.

Another embodiment relates to a dressing assembly wherein the first half of the coupling comprises a female component and the second half of the coupling comprises a male component.

Another embodiment relates to a dressing assembly wherein the filter comprises a dye configured to be released when wet so as to indicate exposure of the filter to fluid.

Another embodiment relates to a dressing assembly wherein the filter comprises activated charcoal as a mixture or a layer, the activated charcoal configured to improve absorbency of the filter as well as reduce dressing odor.

At least one embodiment relates to a filter and tubing assembly for a NPWT dressing with the filter and tubing assembly including a first length of tubing, with the first length of tubing including a first end configured to be coupled to a therapy unit, and a second end comprising a first coupling half. The filter and tubing assembly also includes a second length of tubing including a first end configured to be coupled to a wound dressing and a second end comprising a second coupling half, wherein the second coupling half is configured to mate via a mating interface with the first coupling half, as well as a filter including a sintered polymer and a superabsorbent material, the filter disposed within the second length of tubing or the second coupling half.

Another embodiment relates to a filter and tubing assembly for a NPWT dressing wherein the filter comprises a mixture of polyethylene and a super absorbing polymer, and is configured to perform as a gel-block when wet so as to prevent fluid from migrating through the filter.

Another embodiment relates to a filter and tubing assembly for a NPWT dressing wherein the first coupling half comprises a female component and the second coupling half comprises a male component.

Another embodiment relates to a filter and tubing assembly for a NPWT dressing wherein the filter comprises a dye configured to be released when wet so as to indicate exposure of the filter to fluid.

Another embodiment relates to a filter and tubing assembly for a NPWT dressing wherein the filter comprises activated charcoal as a mixture or a layer.

At least one embodiment relates to a method of making a wound dressing including providing a wound interface layer configured to overlay a wound bed, providing an absorbent layer over the wound interface layer and a drape with the drape positioned over the absorbent layer, and attaching a low-pressure interface on the drape. The method of making a wound dressing further includes coupling a length of tubing having an inline connector to the low-pressure interface, and installing an inline filter including a sintered polymer and a superabsorbent material within the length of tubing or the inline connector.

Another embodiment relates to a method of making a wound dressing wherein the inline filter comprises a mixture of polyethylene and a super absorbing polymer, and is configured to perform as a gel-block when wet so as to prevent fluid from migrating through the inline filter.

Another embodiment relates to a method of making a wound dressing wherein the inline filter comprises activated charcoal as a mixture or a layer, the activated charcoal configured to improve absorbency of the inline filter as well as reduce dressing odor.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Figure 1:
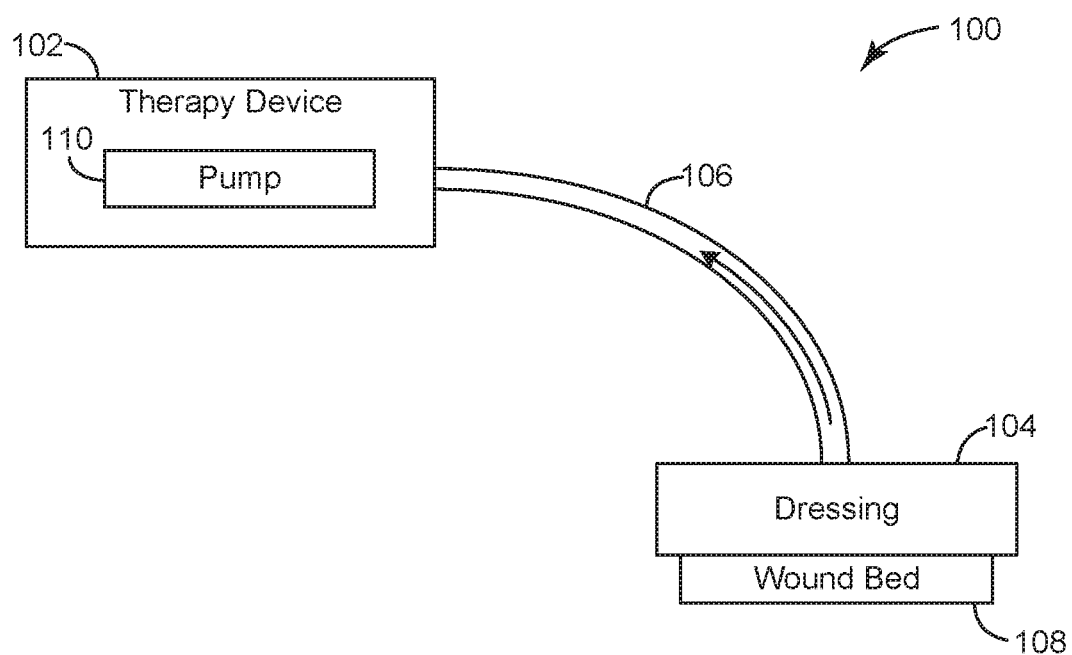
FIG. 1 is a block diagram of a negative pressure wound therapy (NPWT) system, according to an exemplary embodiment.

Referring now to FIG. 1, an exemplary embodiment of a negative pressure wound therapy (NPWT) system 100 is shown. NPWT system 100 includes a therapy device 102 pneumatically communicable with a dressing 104 via tube 106. Dressing 104 is shown as sealed over a wound bed 108. Wound bed 108 is a tissue wound of a patient, for example a laceration, burn, sore, trauma wound, chronic wound, etc. Dressing 104 allows a negative pressure to be maintained at wound bed 108 while absorbing fluid from wound bed 108.

Therapy device 102 includes a pump 110. Pump 110 is operable to pump air out of dressing 104 via tube 106 to create and maintain a negative pressure at wound bed 108. In some embodiments, pump 110 is electrically powered and therapy device 102 includes power systems and control circuitry to power and control operation of the pump 110. In some embodiments, pump 110 is manually-powered, such that a user may manipulate pump 110 to draw air out of dressing 104 as desired by the user. For example, pump 110 may be spring-loaded to gradually pull air from dressing 104 for a duration of time following a compression of pump 110 by the user.

NPWT system 100 shown in FIG. 1 may include additional or alternative components. For example, in some embodiments, tube 106 may include multiple pieces of tubing coupled together in order to facilitate additional function of NPWT system 100. NPWT system 100 may include one or more filters configured between dressing 104 and therapy device 102, with said filters configured to provide a fluid block within NPWT system 100 and prevent fluid from reaching therapy device 102.

Figure 2:
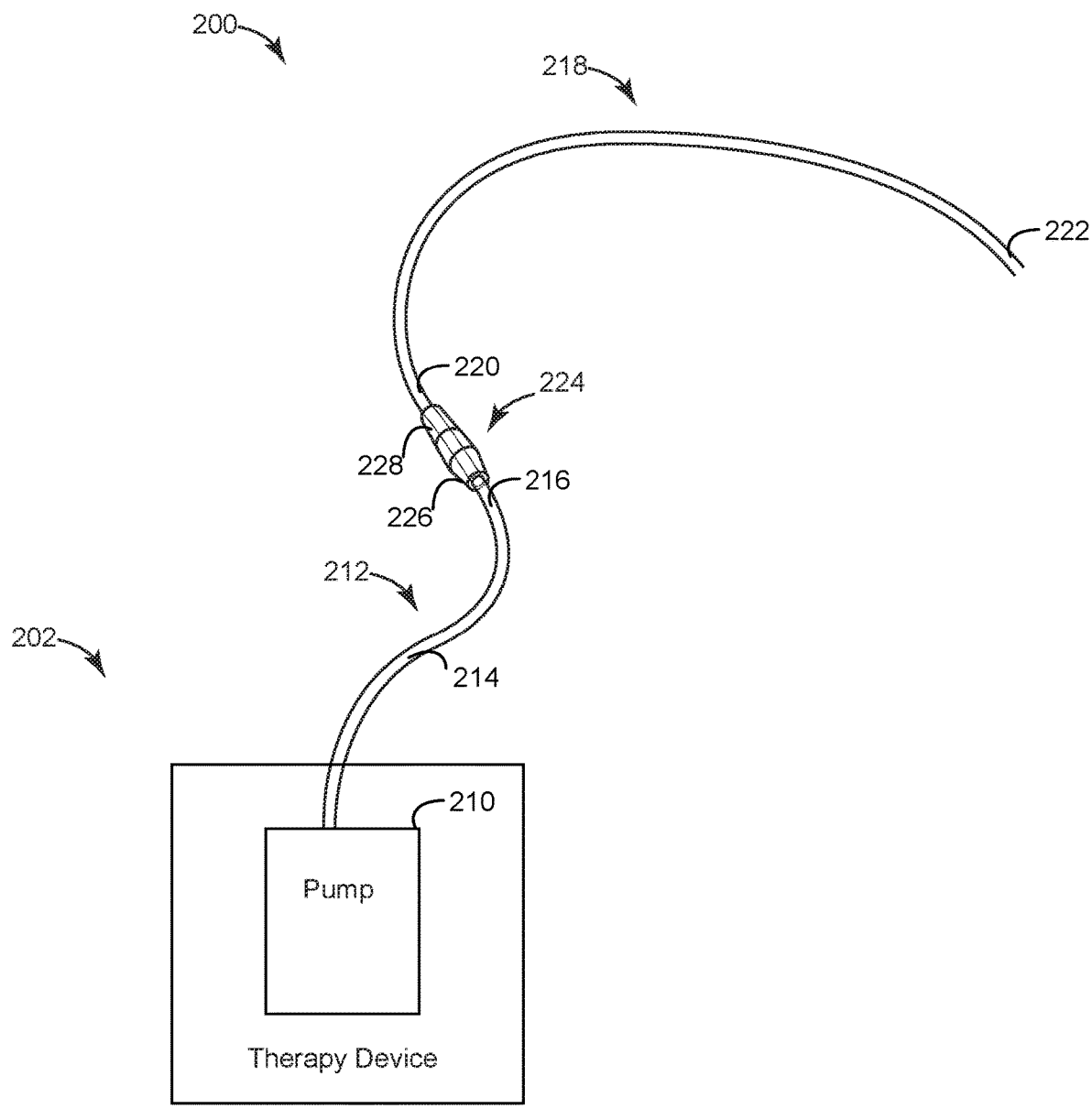
FIG. 2 is a perspective view of a NPWT system, according to an exemplary embodiment.

Referring now to FIG. 2, a system 200 for providing negative pressure wound therapy (NPWT) is shown. System 200 may be similar to and include similar components to NPWT system 100 of FIG. 1. System 200 is shown to include a therapy unit 202. Therapy unit 202 is coupled to and pneumatically communicable with a first tubing 212. In some embodiments, first tubing 212 is releasably coupled to therapy unit 210. Therapy unit 210 may be a pump similar to pump 110 of FIG. 1. Therapy unit 210 may also be a mobile therapy unit, for example a portable therapy unit configured to run on battery power, or may be a stationary therapy unit.

First tubing 212 is shown to include a first end 214 and second end 216. First end 214 of first tubing 212 is coupled to therapy unit 202 such that an airtight seal is formed. First end 214 of first tubing 212 may include one or more retention mechanisms configured to facilitate coupling and airtight sealing with therapy unit 202 which is to say that therapy unit 202 may have complimentary retaining components. Second end 216 of first tubing 212 is configured opposite first end 214. Second end 216 of first tubing 212 is coupled to an inline coupling 224. Inline coupling 224 includes a first coupling portion 226 and a second coupling portion 228, with first coupling portion 226 configured to receive second end 216 of first tubing 212, with first coupling portion 226 and inline coupling 224 forming an airtight seal with second end 216 of first tubing 212. In some embodiments, first end 214 of first tubing 212 may include one or more coupling and/or retention mechanisms. Inline coupling 224 is configured to retain second end 216 of first tubing 212 there within and form an airtight seal with second end 216 of first tubing 212. Inline coupling 224 and/or first coupling portion 226 may include one or more retaining mechanisms configured to mate with second end 216 of first tubing 212 in order to facilitate coupling and said airtight sealing, for example threading, protrusions, or recesses complimentary to components of second end 216 of first tubing 212. First tubing 212 may vary in length and/or diameter in order to accommodate different models of therapy unit 210 and provide different forms of treatment to a patient.

Second coupling portion 228 is configured opposite inline coupling 224 from first coupling portion 226. Second coupling portion is configured to receive a first end 220 of a second tubing 218 as shown in the exemplary embodiment of FIG. 2. Inline coupling 224 and second coupling portion 228 form an airtight seal with first end 220 of second tubing 218 similar to that formed by inline coupling 224 and first coupling portion 226 about second end 216 of first tubing 212. Both first end 220 of second tubing 218 and second coupling portion 228 may include one or more retaining mechanisms the same as or similar to that of second end 216 of first tubing 212 and first coupling portion 226 so as to facilitate coupling with first end 220 of second tubing 218 and promote formation of an airtight seal. In some embodiments, second coupling portion 228 may be configured the same as or similar to first coupling portion 226 and may vary similarly in length and diameter. Additionally, second tubing 218 may vary in length and/or diameter similar to first tubing 212.

In some embodiments, a filter may be configured within one or more of second end 216 of first tubing 212, inline coupling 224, first coupling portion 226, second coupling portion 228, and first end 220 of second tubing 218. The filter may include dimensions that ensure a secure fit within one or more of the previously mentioned components, and may be inserted therein. Additionally, the filter may be configured to allow airflow therethrough when dry, but perform a "gel-block" upon coming in contact with fluid thus restricting or preventing fluid from moving beyond the filter. "Gel-block" is intended to refer to polymeric materials configured to absorb fluid and increase in volume, with the increase in volume effectively blocking a tubing and preventing further movement of fluid.

Second tubing 218 further includes a second end 222, with second end 222 configured opposite second tubing 218 from first end 220. Second end 222 of second tubing 218 is configured to couple with a portion of a wound dressing such as dressing 104 of FIG. 1 (wound dressing not shown in FIG. 2). In coupling with a wound dressing (with wound dressing sealed over a wound bed such as wound bed 108 of FIG. 1), second end 222 of second tubing 218 forms an airtight seal with said wound dressing thus establishing pneumatic communication between therapy unit 210 and a wound bed through a series of sealed components.

Figure 3:
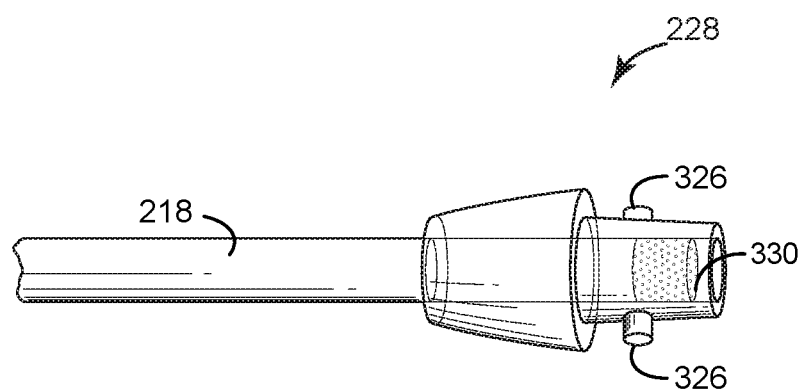
FIG. 3 is side view of a system for fluid ingress protection for a NPWT system, according to an exemplary embodiment.

Referring now to FIG. 3, a system for fluid ingress protection for a NPWT device is shown, according to an exemplary embodiment.

The system for fluid ingress protection includes second tubing 218 (as shown in FIG. 2) and second coupling portion 228. As shown in the exemplary embodiment of FIG. 3, second coupling portion 228 is configured about a portion of second tubing 218. Second tubing 218 may vary in diameter in some embodiments with second coupling portion 228 varying proportionally. Second coupling portion 228 may have one or more substantially conical geometries extending and expanding in a single or opposite directions from one another. Second coupling portion 228 is further configured to include a retaining mechanism 326. Retaining mechanism 326 is configured to mate with a complimentary retaining mechanism of an additional component, such as an inline coupling, to facilitate formation of an airtight seal. In the exemplary embodiment of FIG. 3, retaining mechanism 326 is shown as a pair of protrusions extending at a substantially orthogonal angle from the surface of second tubing 218. In alternative embodiments, retaining mechanism 326 may include one or more recesses or threading.

In coupling with an additional component, second coupling portion 228 is configured to interface with said additional component. In some embodiments, second coupling portion 228 may be received by the additional component with retaining mechanism 326 mating with a complimentary retaining mechanism thereof. Second coupling portion 228 may be configured to abut any additional component. Second coupling portion 228 is further configured to promote the formation of an airtight seal between the system of FIG. 3 and any additional component so as to facilitate negative pressure wound therapy for a patient.

The system of FIG. 3 includes a filter 330 disposed within second coupling portion 228. Filter 330 is configured to permit airflow, for example from a NPWT system. However, when contacted by fluid, filter 330 is configured to obstruct any flow of fluid effectively forming a block within second tubing 218. For example, if a fluid were to contact the portion of filter 330 nearest a wound dressing, such as dressing 104 of FIG. 1, a block would be formed preventing flow of fluid to the remaining portion of second tubing 218 not yet exposed to fluid as well as any subsequent tubing attached downstream. In some embodiments, filter 330 may block second tubing 218 by performing a "gel-block" as a means of preventing fluid from migrating through filter 330. A "gel-block" refers to the porous filter structure, configured within filter 330 and further configured to absorb fluid upon contact. The absorption of fluid causes a gelling agent material to expand and assume a gel-like consistency, effectively eliminating the porous quality of the material. The expansion eliminates the porosity of the filter and occupies the diameter of tubing such as second tubing 218, preventing the migration or passage of any liquid beyond the filter.

According to one embodiment filter 330 is hydrophobic and comprises a sintered polymer polythene, which incorporates (or is impregnated with) a gelling agent to ensure the formation of a complete seal upon contact with fluid. Filter 330 may further comprise a mixture of polythene and a super absorbing polymer (SAP) and/or other superabsorbent materials or materials with superabsorbent properties. In some embodiments, filter 330 may comprise a Porex material, for example part number XS-5070 or XM-1777. Filter 330 may also comprise a dye, with the dye configured to be released upon contact with fluid within second tubing 218 for example, to indicate to healthcare providers the presence of fluid in contact with filter 330. Filter 330 may further comprise activated charcoal, which may be configured as a coating, a layer of, or added to the mixture of filter 330 so as to reduce dressing odor when dry. Such an addition of activated charcoal may also improve absorbency of filter 330 and thus fluid blocking/scaling ability, as well as increasing breakthrough pressure of filter 330. Filter 330 may be generally configured to absorb small amounts of fluid after contact while simultaneously blocking larger amounts of fluid from migrating past or through filter 330. In some embodiments, absorbency of filter 330 may recover after contact with a fluid.

In some embodiments, filter 330 may include a length ranging from approximately 2 mm to 8 mm as well as a diameter ranging from approximately 3 mm to 5 mm. It should be noted that filter 330 can be configured according to second tubing 218 and any geometry and/or dimensions thereof in order to from a tight interference fit once placed. In alternative embodiments, filter 330 may further include combinations of porous polymer material of approximately 250 microns and 7 mm of, for example Luquasorb absorbent granules, within tubing such as second tubing 218 in order to maintain airflow while providing fluid blockage upon contact with any fluid. Some other embodiments may include the aforementioned porous polymer material decreased to approximately 1 mm. In some embodiments, filter 330 may include an average pore size ranging from approximately 20-60 micrometers with one side of a given sheet rough and one side of a given sheet smooth. Other properties of filter 330 may include accommodating an airflow ranging from approximately 160-480 ml/min at a set inlet pressure of approximately 1.2" water with test disc measurement of approximately 19 mm (e.g., PA 02-07), a target density ranging from approximately 0.51-0.59 g/cm$^3$, a tensile strength greater than approximately 1.3 N/mm$^2$, and an embedded contamination no greater than approximately 1.6 mm. Additionally, surface imperfection excluding embedded contamination may not exceed approximately 5% of surface area. Possible materials of filter 330 also may not have guaranteed air distribution. Filter 330 may further comprise polytetrafluoroethylene (PTFE). Filter 330, in various configurations and different embodiments, may also be applicable or adapted for use in other applications in which a risk of fluid ingress may be detrimental to a device.

In some embodiments, filter 330 may be disposed within a coupling component separate from and/or adjacent to a piece of tubing such as second tubing 218, for example a male component of a coupling mechanism. Filter 330 may also be configured on a dressing-side (not shown, but similar to that of FIG. 1) of a coupling component, which is to say between a coupling component and a patient rather than between a coupling component and a therapy device. In other embodiments filter 330 may be disposed at various points between a wound dressing and a therapy device (such as dressing 104 and therapy device 102, respectively, of FIG. 1). Filter 330 may be placed, whether within second tubing 218, a coupling portion as mentioned, or other component by a compression tool. In some embodiments, filter 330 may have a tapered geometry on one end. An anti-bacterial agent may also be introduced to filter 330 in order to provide added protection against contamination of a therapy device such as therapy unit 210 of FIG. 2. Antibacterial protection may also be introduced elsewhere in the system of FIG. 3. Additionally, filter 330 may be configured to have a low-profile design, which is to say that filter 330 may be disposed within second tubing 218 as shown in the exemplary embodiment of FIG. 3 or a coupling device, for example. Filter 330 may be configured further to withstand manipulation due to normal patient and movement patterns which may include, for example bumping and jostling as well as being sat on by a patient, while maintaining the aforementioned fluid ingress protection properties. That is to say that filter 330 may be flexible, such as within tubing similar to second tubing 218, or within a rigid connector such as a coupling component. Filter 330 may also be installed at multiple locations within a system, such as NPWT system 100 of FIG. 1, system 200 of FIG. 2, as well as other similar NPWT systems.

Figure 4A:
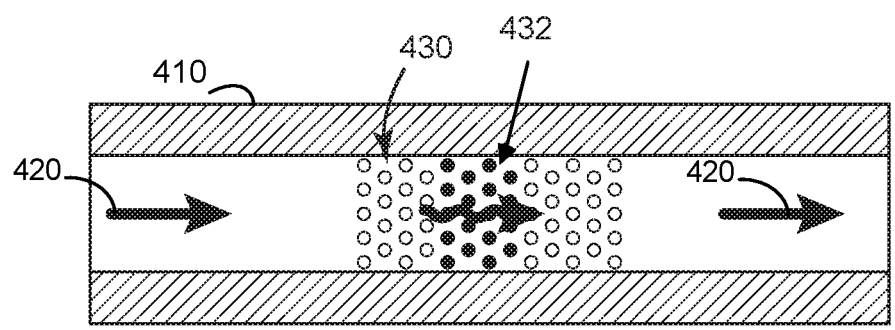
FIG. 4A is a schematic diagram of a system for fluid ingress protection for a NPWT system, according to an exemplary embodiment.

Referring now to FIG. 4A, a schematic diagram of a system for fluid ingress protection system is shown to include airflow through "non-activated granules", according to an exemplary embodiment. Granules of FIG. 4A may be a super absorbent polymer portion of filter 330 of FIG. 3. The system of FIG. 4A may be exemplary of a NPWT system such as those shown in FIGS. 1-3, as well as other similar NPWT systems. In the exemplary embodiment of FIG. 4, fluid has not been introduced to the filter. A tubing 410 (which may be the same as or similar to second tubing 218 of FIG. 3 or tubing shown in other previous embodiments) is shown to include an airflow 420. Airflow 420 is shown to move into and through tubing 410. Airflow 420 is further shown to contact a filter, shown as filter 430. Filter 430 may be the same as or similar to one or more possible embodiments of filter 330 of FIG. 3. As airflow 420 encounters filter 430, airflow 420 is permitted to migrate through filter 430. An inactivated portion 432 of filter 430 is further shown to permit ingress of airflow 420 through filter 430 and along tubing 410. In the event of fluid contacting filter 430, inactivated portion 432 would become activated so as to initiate a gel-block and block tubing 410 and prevent fluid from migrating through filter 430. It should be noted that, as shown in FIG. 4A, filter 430 has not been in contact with and fluid.

Figure 4B:
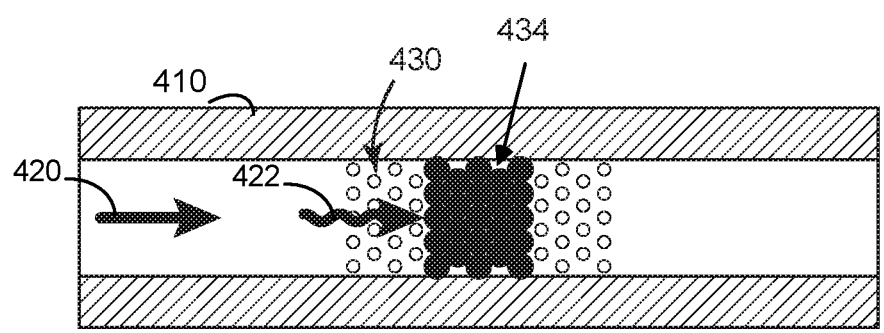
FIG. 4B is an alternative schematic diagram of a system for fluid ingress protection for a NPWT system, according to an exemplary embodiment.

Referring now to FIG. 4B, a schematic diagram of the system of FIG. 4A is shown to include fluid ingress, which causes the granules to swell and obstruct flow. In FIG. 4B, airflow 420 is shown to enter tubing 410 after a fluid 422 has already entered said tubing 410. Fluid 422 is shown to contact filter 430. Filter 430 includes an activated portion 434 (which may be the same or similar to portions of filter 330 of FIG. 3), which becomes activated by contact with fluid 422, shown to absorb the fluid 422 upon contact and provide a block (for example, a gel-block) within tubing 410 such that fluid 422 is not permitted to migrate through filter 430. By absorbing fluid 422 and providing a block within tubing 410, activated portion 434 prevents fluid 422 from migrating through filter 430 and ultimately reaching a therapy device (not shown) to which fluid 422 may cause contamination. In some embodiments, after contact with fluid 422, filter 430 and/or tubing 410 may be may be replaced.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

It is important to note that the construction and arrangement of the [apparatus, system, assembly, etc.] as shown in the various exemplary embodiments is illustrative only. Additionally, any element disclosed in one embodiment may be incorporated or utilized with any other embodiment disclosed herein.

What is claimed is:

1. A filter and tubing assembly for a negative pressure wound treatment (NPWT) dressing, the filter and tubing assembly comprising:
    a first length of tubing comprising:
        a first end configured to be coupled to a therapy unit, and
        a second end comprising a first coupling half;
    a second length of tubing comprising:
        a first end configured to be coupled to a wound dressing, and
        a second end comprising a second coupling half, wherein the second coupling half is configured to mate via a mating interface with the first coupling half; and
    a filter comprising a sintered polymer and a superabsorbent material, the filter having a density between 0.51 g/cm$^3$ and 0.59 g/cm$^3$ and being disposed within the second length of tubing or the second coupling half.

2. The filter and tubing assembly of claim 1, wherein the filter comprises a mixture of polyethylene and a super absorbing polymer (SAP), the filter configured to perform as a gel-block when wet to prevent fluid from migrating through the filter.

3. The filter and tubing assembly of claim 1, wherein the first coupling half comprises a female component and the second coupling half comprises a male component.

4. The filter and tubing assembly of claim 1, wherein the filter comprises a dye configured to be released when wet to indicate exposure of the filter to fluid.

5. The filter and tubing assembly of claim 1, wherein the filter comprises activated charcoal as a mixture or a layer.

6. A method of making a wound dressing, comprising:
    providing a wound interface layer configured to overlay a wound bed;
    providing a dressing over the wound interface layer, the dressing having an absorbent layer and a drape, the drape positioned over the absorbent layer;
    attaching a low-pressure interface on the drape;
    coupling a length of tubing having an inline connector to the low-pressure interface; and
    installing an inline filter comprising a sintered polymer and a superabsorbent material within the length of tubing or the inline connector, the inline filter including a density between 0.51 g/cm$^3$ and 0.59 g/cm$^3$.

7. The method of claim 6, wherein the inline filter comprises a mixture of polyethylene and a super absorbing polymer (SAP), the inline filter configured to perform as a gel-block when wet to prevent fluid from migrating through the inline filter.

8. The method of claim 6, wherein the inline filter comprises activated charcoal as a mixture or a layer, the activated charcoal configured to improve absorbency of the inline filter as well as reduce dressing odor.

* * * * *